US011058381B2

(12) United States Patent
Sutter

(10) Patent No.: US 11,058,381 B2
(45) Date of Patent: Jul. 13, 2021

(54) METHOD FOR OPERATING AN X-RAY DEVICE, X-RAY DEVICE, COMPUTER PROGRAM AND ELECTRONICALLY READABLE DATA CARRIER

(71) Applicant: Siemens Healthcare GmbH, Erlangen (DE)

(72) Inventor: Sven-Martin Sutter, Herzogenaurach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 3 days.

(21) Appl. No.: 16/542,707

(22) Filed: Aug. 16, 2019

(65) Prior Publication Data
US 2020/0069272 A1 Mar. 5, 2020

(30) Foreign Application Priority Data
Aug. 28, 2018 (EP) .................................. EP18191078

(51) Int. Cl.
*A61B 6/00* (2006.01)
*A61B 6/12* (2006.01)
*G16H 30/40* (2018.01)
*A61B 34/30* (2016.01)
*A61B 90/00* (2016.01)

(52) U.S. Cl.
CPC .............. *A61B 6/487* (2013.01); *A61B 6/405* (2013.01); *A61B 6/465* (2013.01); *A61B 6/504* (2013.01); *A61B 6/542* (2013.01); *A61B 6/12* (2013.01); *A61B 6/466* (2013.01); *A61B 2034/301* (2016.02); *A61B 2090/376* (2016.02); *G16H 30/40* (2018.01)

(58) Field of Classification Search
None
See application file for complete search history.

(56) References Cited

U.S. PATENT DOCUMENTS

2010/0128955 A1* 5/2010 Walimbe .............. A61B 6/5247
382/132
2011/0170662 A1* 7/2011 Baumgart .............. A61B 6/545
378/62
2013/0182822 A1* 7/2013 Sakaguchi ............. A61B 6/022
378/42

(Continued)

FOREIGN PATENT DOCUMENTS

DE 102009015830 A1 10/2010
WO WO 2017106177 A1 6/2017

OTHER PUBLICATIONS

NPL: Extended European Search report for EP Application No. 18191078.7, dated Aug. 3, 2019 and English translation herewith.

*Primary Examiner* — Hoon K Song
(74) *Attorney, Agent, or Firm* — Harness, Dickey & Pierce, P.L.C.

(57) ABSTRACT

A method is for operating an x-ray device for recording a series of images, in particular for fluoroscopic monitoring of a recording region of a patient. The method includes acquiring fluoroscopy images of a patient with a recording rate and a recording dose; and displaying the fluoroscopy images acquired to a user on a display device at a frame rate. The recording dose is selected automatically as a function of a change in image contents between consecutive fluoroscopy images acquired.

16 Claims, 2 Drawing Sheets

(56) References Cited

U.S. PATENT DOCUMENTS

| | | |
|---|---|---|
| 2015/0139385 A1 | 5/2015 | Bone et al. |
| 2015/0139395 A1 | 5/2015 | Yi et al. |
| 2015/0374323 A1 | 12/2015 | Shiraishi et al. |
| 2017/0281114 A1 | 10/2017 | Riddell et al. |
| 2018/0360398 A1* | 12/2018 | Wenderow ............. G16H 30/40 |

* cited by examiner

METHOD FOR OPERATING AN X-RAY DEVICE, X-RAY DEVICE, COMPUTER PROGRAM AND ELECTRONICALLY READABLE DATA CARRIER

PRIORITY STATEMENT

The present application hereby claims priority under 35 U.S.C. § 119 to European patent application number EP 18191078.7 filed Aug. 28, 2018, the entire contents of which are hereby incorporated herein by reference.

FIELD

Embodiments of the invention generally relate to a method for operating an x-ray device for recording a series of images for, in particular, fluoroscopic monitoring of a recording region of a patient, wherein fluoroscopy images are acquired with a recording rate and a recording dose and are shown to a user on a display device with a frame rate. In addition, embodiments of the invention generally relate to an x-ray device, a computer program and an electronically readable data carrier.

BACKGROUND

X-ray imaging is frequently used in the prior art to monitor dynamic processes in a recording region within a patient. Examples of dynamic processes of this type are what are known as roadmap procedures, in which a medical instrument, for instance a catheter or a guidewire, is to be moved within a patient to a target position so that the patient is compromised as little as possible. Another example are imaging processes using contrast agent, in which, for instance, the contrast agent distribution is to be monitored by fluoroscopy images. With such monitoring processes, fluoroscopy images of the patient are recorded with a specific recording rate and are displayed immediately or after a specific postprocessing, this means that showing the fluoroscopy images on a display device does not necessarily exclude a previous processing of the fluoroscopy images. It is known, for instance, to highlight specific features, for instance the medical instrument to be traced, and suchlike. While the best-known recording technique, in which a series of images is recorded to monitor a recording region of a patient, is fluoroscopy, other approaches are also conceivable, for instance when recording series of images of digital radiographies.

When a series of fluoroscopy images is recorded for monitoring, the patient is, in effect, almost continuously exposed to the x-ray radiation, so that the reduction in dose for the patient is an important aspect in such monitoring procedures, in particular fluoroscopy. In this context, various possibilities were already proposed, in order to reduce or minimize the dose exposure for a patient. Firstly, such fluoroscopy images used for monitoring purposes are in most cases produced with the smallest possible recording dose, since the relevant features to be observed, for instance contrast agent and/or medical instruments, are also imaged sufficiently clearly with low doses. In order, additionally, to obtain a sufficiently accurate representation of the anatomy, it was proposed to carry out pre-interventional image data, for instance, clearly indicating a superimposition of fluoroscopy images or display images derived therefrom with the anatomy of the patient. It was also proposed to only collimate the radiation field on the crucial region.

In a further approach, likewise known in the prior art, it was proposed to reduce the recording rate of the fluoroscopy images if there is no change or only a slight change from one fluoroscopy image to another. To this end, a degree of the change in the image contents between the two most up to date fluoroscopy images can be determined and compared with a rearrangement threshold, in order to switch back, for instance, from a base recording rate of 30 fps to a recording rate of 10 fps or less. If more significant changes in the image contents then occur again between the most up to date fluoroscopy images, it is possible to switch back again to the quicker recording rate, in other words, for instance, the base recording rate. By switching over between different recording rates, the frame rate, with which the image data of the fluoroscopy images is shown, also changes.

This approach is disadvantageous in that it is not possible to respond to or also not sufficiently quickly to sudden, rapidly occurring changes in the image contents, so that the user may miss out on essential information or said information may not be identifiable with the adequate quality.

SUMMARY

At least one embodiment of the invention therefore specifies a possibility of reducing the dose for the patient when a series of images is recorded for monitoring purposes, which still enables a quick reaction to more significant changes in image contents which occur.

To achieve this, there is provision in accordance with at least one embodiment of the invention in a method for the recording dose to be automatically selected as a function of a change in image contents between the current, consecutive fluoroscopy images. In particular, with more minimal changes in image contents, a lower recording dose can be selected than with more significant changes in image contents.

At least one embodiment of the invention relates to a method for operating an x-ray device for recording a series of images for in particular fluoroscopic monitoring of a recording region of a patient, wherein fluoroscopy images are acquired with a recording rate and a recording dose and are displayed to a user on a display device with an frame rate, characterized in that the recording dose is selected automatically as a function of a change in image contents between the current consecutive fluoroscopy images.

At least one embodiment of the invention relates to a method for operating an x-ray device for recording a series of images of a patient, the method comprising:
 acquiring fluoroscopy images of a patient with a recording rate and a recording dose; and
 displaying the fluoroscopy images acquired to a user on a display device at a frame rate, the recording dose being selected automatically as a function of a change in image contents between consecutive fluoroscopy images acquired.

In addition to the method, at least one embodiment of the invention also relates to an X-ray device which, in addition to at least one recording arrangement having an X-ray emitter and an X-ray detector, also has a control device configured for carrying out the method according to at least one embodiment of the invention.

At least one embodiment of the invention also relates to an X-ray device x-ray device, comprising:
 a controller (including at least one processor for example), operatively connected to a storage device (such as a memory for example), to:
  acquire fluoroscopy images of a patient at a recording rate and a recording dose; and a display device to display the fluoroscopy images acquired to a user at a frame rate, the recording dose being selected automatically as a function of a change in image contents between consecutive fluoroscopy images acquired.

In this regard, the control device can also be embodied to otherwise control operation of the x-ray device, and have at least one processor and one storage device, such as a memory for example. In particular, the control device for carrying out at least one embodiment of the inventive method can, in addition to a recording unit for controlling the recording operation of the x-ray device, also comprise a comparison unit for determining a change in image contents and an adjustment unit for adjusting the recording dose. Furthermore, in a preferred embodiment of the invention, a combination unit for combining a number of fluoroscopy images recorded consecutively with a reduced recording dose can also be used to form a display image. The x-ray device further comprises the display device, for instance a monitor, on which the fluoroscopy images, possibly sometimes combined to form a display image, are output.

A computer program according to at least one embodiment of the invention can, for example, be loaded directly into a memory of a control device of an x-ray device, and has program code/segments for carrying out the steps of a method according to at least one embodiment of the invention when the computer program is executed in the control device of the x-ray device.

An inventive electronically readable data carrier according to at least one embodiment of the invention comprises electronically readable control information stored thereon, which control information comprises at least one computer program according to at least one embodiment of the invention and is designed such that it performs a method according to at least one embodiment of the invention when the data carrier is used in a control device of an x-ray device. The data carrier can be, in particular, a non-transient data carrier, for example, a CD-ROM.

At least one embodiment of the invention also relates to a non-transitory computer program product, storing a computer program to, when executed by a controller of an x-ray device, performs the method of at least one embodiment.

At least one embodiment of the invention also relates to a non-transitory electronically readable data carrier, storing a computer program to, when executed by a controller of an x-ray device, performs the method of at least one embodiment.

BRIEF DESCRIPTION OF THE DRAWINGS

Further advantages and details of the present invention are disclosed in the example embodiments described below and by reference to the drawings, in which.

DETAILED DESCRIPTION OF THE EXAMPLE EMBODIMENTS

Figure 1:
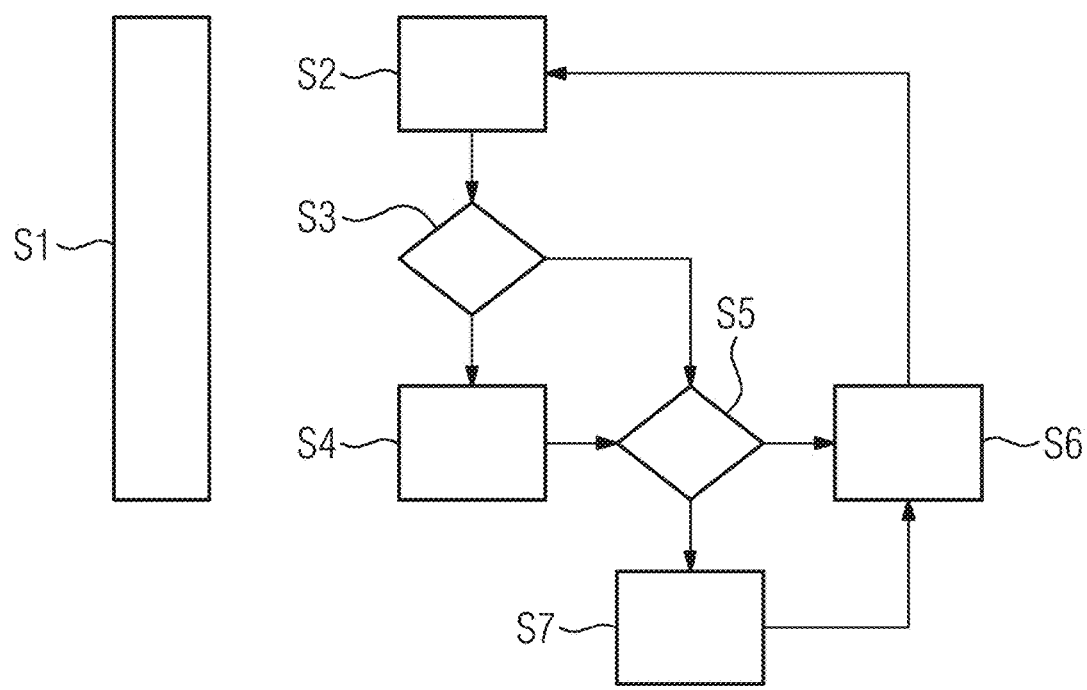
FIG. 1 shows a general flow diagram of an example embodiment of the inventive method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally)

between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In order to be able to respond as quickly as possible to sudden changes in image content of a more significant type, in particular with an increase in the frame rate shown on the display device, it is proposed not to reduce the recording rate itself with low-grade changes in the image contents, but instead to dynamically adjust the recording dose, in particular the recording dose per fluoroscopy image such that changes to relevant image contents of this type can still be established extremely quickly, but the quality of the fluoroscopy images reduces significantly per se.

In this context, a particularly advantageous development of at least one embodiment of the present invention provides that with a reduction in the recording dose from in each case a number of fluoroscopy images recorded consecutively, a display image, which corresponds to a maximum, usable base dose, is determined and output on the display device. In this way provision can be made for the fluoroscopy images to be combined to form the display image by way of adding. This means that the reduction in the frame rate, to which the operator of the known procedures is accustomed, which at least involves the display on the display device, can also still take place.

To this end, provision can be made for the frame rate to be reduced when display images are determined, in particular by a factor according to the number of combined fluoroscopy images with disjointed groups of combined fluoroscopy images. In other words, the recording dose can expediently be reduced so that a number of fluoroscopy images have to be combined, in particular added, before these can be shown again on the display device with sufficient quality.

The operator therefore has the image impression known to him, but additionally also preferably the frame rate changeover known to him. In this regard, blocks/groups of consecutively recorded fluoroscopy images are finally always combined to form a display image, in particular by way of adding, so that in each case after recording a number of fluoroscopy images to be combined, a new display image can be output, so that the frame rate reduces by a factor which corresponds to the number of fluoroscopy images to be combined.

In spite of this particularly preferred combination of fluoroscopy images to form a display image, the control device of the x-ray device individually analyses the fluoroscopy images recorded with the reduced recording dose, which concerns changes in the image contents, and possibly readjusts the recording dose, in particular for renewed increase to the base dose, namely to the base dose, provided adequately significant changes in image contents occur.

In summary, it is thus proposed in at least one embodiment, to adjust the recording dose per fluoroscopy image in accordance with the dynamic change in image contents from fluoroscopy image to fluoroscopy image with sequence recordings and in particular also to select the image display frequency, in other words the frame rate, accordingly on the display device. Therefore the control device of the x-ray device can react quickly to dynamic changes in image contents, for instance after injecting a contrast agent bolus and/or with a quicker movement of a medical instrument in the recording region.

In a particularly preferred development of at least one embodiment of the invention, provision can be made for the recording dose also to be selected as a function of a gradient of the change in image contents by way of more than two current fluoroscopy images recorded consecutively. A type of speed of the change in image contents is finally included in the observations. In this way, a future minimum change in image contents can be predicted by taking into account the change in image contents gradients and the new recording dose can be selected as a function hereof.

For this purpose, a prediction algorithm can be used, for instance, which can be selected in particular depending on application, can therefore be geared for instance toward typical propagation speeds of contrast agent, which penetrates the recording area, and/or can assess typical working speeds with medical instruments, in particular at different points in the workflow. In this way machine learning techniques, or generally artificial intelligence, can also be used.

Reference should be made at this point to the fact that it is essentially also conceivable to assign recording doses corresponding to changes in image contents or changes in image contents intervals, in particular in an application-related manner, for instance in a look-up table or by way of a mathematical relationship.

It is particularly expedient, within the scope of at least one embodiment of the present invention, however, if the change in the recording dose is carried out in discrete stages as a function of the at least one rearrangement threshold being exceeded or not met by the change in image contents. These stages can then in particular be selected such that by combining, in particular adding, an integer number of fluoroscopy images recorded consecutively, there is the impression that the resulting display image has been recorded with the base dose, so that, except for possibly slightly increased noise, the image impression of the base dose for the user is retained as easily as possible, in particular by reducing the frame rate on the display device.

Stages of the recording dose can therefore be selected in a targeted manner so that by combining, in particular by adding, the consecutive fluoroscopy images of a group, there is again the impression of recording using a base dose. It is in particular conceivable here to reduce the recording dose by an integer factor on the basis of the base dose, so that by adding a number of fluoroscopy images which corresponds to the integer factor, the suitable display image is produced.

In a simple example embodiment, two stages can then be provided, consequently two discrete recording doses. In one such case, provision can be made, when fulfilling a change in image contents, dropping below a first rearrangement threshold, between reduction criterion indicating consecutive images, for the recording dose to be reduced on the basis of the base dose and that, when an increase criterion is fulfilled, which indicates a change in image contents, increasing above a second rearrangement threshold, between consecutive fluoroscopy images, the recording dose is increased again to the base dose. A corresponding adjustment of the frame rates can take place similarly in this simple example embodiment.

In advantageous embodiments, more than two stages, which means more than two discrete values of the recording dose, can be used, however. This is particularly expedient if the recording dose is further to be selected as a function of a change in image contents gradients over more than two current fluoroscopy images recorded consecutively. Provision can then be made for at least one stage to be skipped if a threshold value is exceeded by the change in image contents gradients. The speed of the change in image contents thus indicates that an even more significant change in image contents is to be expected in the future, and at the same time in a further reduction stage the recording dose can be switched over, wherein conversely the same can naturally also apply. However, with two stages, it may also be useful to take the change in image content gradients into account, for instance, in order to be able to promptly reduce the recording dose or increase the recording dose to the base dose.

As a measure of the change in image contents, a comparison measure selected in particular in an application-related manner can be selected between the two most up-to-date fluoroscopy images. In this case, the most different of comparison measures are conceivable overall, for instance with contrast agents by locally analyzing the content of blood vessels, in subsequent medical instruments, the displacement thereof and suchlike. Naturally the image data of the fluoroscopy images of comparison measures to be evaluated globally can also be used, when these only respond adequately sensitively to the relevant changes to the corresponding application.

Provision can specifically be made as an application, for instance, for the fluoroscopy images to be recorded for monitoring a minimally invasive intervention carried out with an instrument, in particular a catheter and/or for monitoring a contrast agent propagation within the patient. Also, in other application cases, in which dynamic changes can occur within a patient, which are to be monitored by way of fluoroscopy images, in particular fluoroscopy images, the present invention can naturally be used.

In addition to the method, at least one embodiment of the invention also relates to an X-ray device which, in addition to at least one recording arrangement having an X-ray emitter and an X-ray detector, also has a control device configured for carrying out the method according to at least one embodiment of the invention.

In this regard, the control device can also be embodied to otherwise control operation of the x-ray device, and have at least one processor and one storage device, such as a memory for example. In particular, the control device for carrying out at least one embodiment of the inventive method can, in addition to a recording unit for controlling the recording operation of the x-ray device, also comprise a comparison unit for determining a change in image contents and an adjustment unit for adjusting the recording dose. Furthermore, in a preferred embodiment of the invention, a combination unit for combining a number of fluoroscopy images recorded consecutively with a reduced recording dose can also be used to form a display image. The x-ray device further comprises the display device, for instance a monitor, on which the fluoroscopy images, possibly sometimes combined to form a display image, are output.

A computer program according to at least one embodiment of the invention can, for example, be loaded directly into a memory of a control device of an x-ray device, and has program code/segments for carrying out the steps of a method according to at least one embodiment of the invention when the computer program is executed in the control device of the x-ray device.

An inventive electronically readable data carrier according to at least one embodiment of the invention comprises electronically readable control information stored thereon, which control information comprises at least one computer program according to at least one embodiment of the invention and is designed such that it performs a method according to at least one embodiment of the invention when the data carrier is used in a control device of an x-ray device. The data carrier can be, in particular, a non-transient data carrier, for example, a CD-ROM.

Example embodiments of the inventive method should be shown below on the basis of fluoroscopic monitoring upon application to a patient, for instance a minimally invasive intervention with a medical instrument. In this regard, an x-ray device is used, which has a recording arrangement, for instance on a C-arm, by way of which fluoroscopy images of a patient can be recorded with an already low base dose as the recording dose, said fluoroscopy recordings adequately showing dynamically changing features to be monitored in the recording area of the patient. A series of fluoroscopy images is therefore recorded here. In order to reduce the patient's dose exposure, with an unchanged recording rate, the recording dose is reduced on the basis of the base dose, and a number of fluoroscopy images is consequently combined to form a display image, in order to further obtain the quality in the displays which corresponds to the base dose, wherein the frame rate on a corresponding display device is reduced.

FIG. 1 shows a general flow chart of an example embodiment of the inventive method. Here step S1 indicates the ongoing monitoring by continuously recording fluoroscopy images of the recording area with the x-ray device, wherein the recording rate is kept constant. Whenever there is a new fluoroscopy image, in a step S2 by comparing the two most up-to-date fluoroscopy images, a measure of a change in image content, in particular application-specific, is determined, currently, by an application-specific comparison measure being applied to the pair of two most up-to-date fluoroscopy images.

This thus determined change in image contents is evaluated in step S3 by at least one evaluation criterion, in order to establish whether an adjustment of the recording dose, in particular a reduction on the basis of the base value, is useful on account of changes only occurring slowly or not at all or whether an increase in the recording dose is useful on the basis of the sudden/quick/more significant changes in image contents having occurred.

If a change in the recording dose is useful, this is carried out in step S4. Here at least two recording doses to be used, preferably more recording doses, are provided in the present example embodiments, wherein the recording doses, to which it can be reduced, correspond to an integer number of the base dose. In particular, different intervals of changes in image contents are assigned specific, discrete values of recording doses. In this context it should be noted that the intervals can naturally in turn be selected as a function of the currently set recording dose, since, in step S2, the two most up-to-date fluoroscopy images are compared with one another, and may look different depending on recording dose and may consequently also result in different values ranges of a comparison measure. In particular, changes in image contents intervals with assigned recording doses are therefore provided for each recording dose, so that the assignment to a specific one of these intervals results in a switchover according to step S4.

A check is carried out in step S5 to determine whether a reduced recording dose, compared with the base dose which shows the maximum recording dose permitted for the fluoroscope, is operated. If this is not the case, step S6 shows the current fluoroscopy image on the display device, so that the frame rate on the display device corresponds in particular to the recording rate.

If, however, a reduced recording dose is operated, in a step S7 a number of fluoroscopy images is combined to form a display image which, in terms of its impression, corresponds to a fluoroscopy image which has been recorded with the base dose. If, for instance, the recording dose, as explained above, has been reduced by a factor k, disjointed groups of k fluoroscopy images are in each case combined to form another display image, which is then shown in step S6.

It is evident that during the collection of fluoroscopy images to be combined in step S2, it is in each case further continuously monitored for the two most up-to-date fluoroscopy images whether a relevant change in image contents is present. This means that even when the frame rate for the display is likewise reduced with a reduced recording dose because display images are only generated every k fluoroscopy images, it is still possible to respond to sudden, significant changes in image contents extremely quickly.

Figure 2:
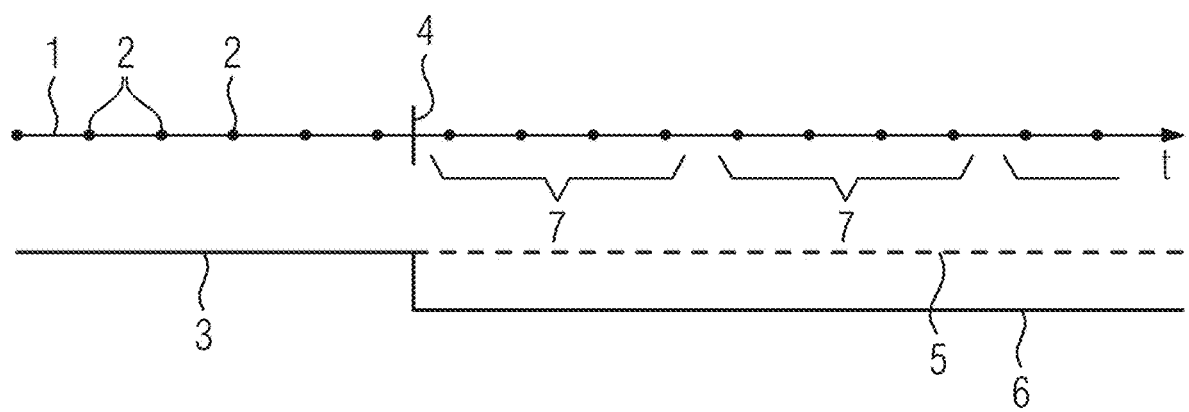
FIG. 2 shows a possible curve of different variables during a fluoroscopy monitoring.

This procedure should be explained in more detail in FIG. 2. A time beam 1 is firstly shown with regular consecutive recording time instants 2 for fluoroscopy images. A curve 3 of the recording dose used is shown below the time beam 1. As is apparent, it was determined at time instant 4 in step S3 that a reduction criterion is fulfilled on account of extremely small changes in image contents, so that the recording dose according to step S4 has been reduced from the base dose 5 to a lower value 6, here a quarter of the base dose 5. From time instant 4, four fluoroscopy images, cf. bracket 7, are therefore always combined, currently added, in accordance with step 7, in order to produce display images so that the frame rate likewise quarters when displayed in step S6. Here the reduction by the factor four is only to be understood as an example.

As already mentioned, here two such stages do not necessarily have to be provided, but instead also three or more. Precisely in this context, but also with the use of just two stages, an expedient, optional development of steps S2 and S3 provides that a gradient of the change in image contents is also additionally determined in step S2 by way of more than two current fluoroscopy images recorded consecutively. For instance, the last two to ten fluoroscopy image pairs recorded can be considered here. Then it is possible to assess whether an occurred change in image contents has been an outlier relating only to the fluoroscopy image pair, for instance, so that an outlier detection can therefore be carried out, wherein with a detected outlier, in particular an individual event, it is not necessary to switch over into step S3. Preferably it is also possible additionally or alternatively, however, to comprehend the change in image contents gradients as a trend, for instance within the meaning of the description of a medical instrument which has rotated, so that, in particular application-related, it is also possible to estimate the level of changes in image contents to which the current dynamic processes amount. As a function of this, one stage of the recording dose can be skipped, for instance, and/or in step S3 an earlier, previewing switchover to another, in particular also higher, recording dose can possibly also take place.

Figure 3:
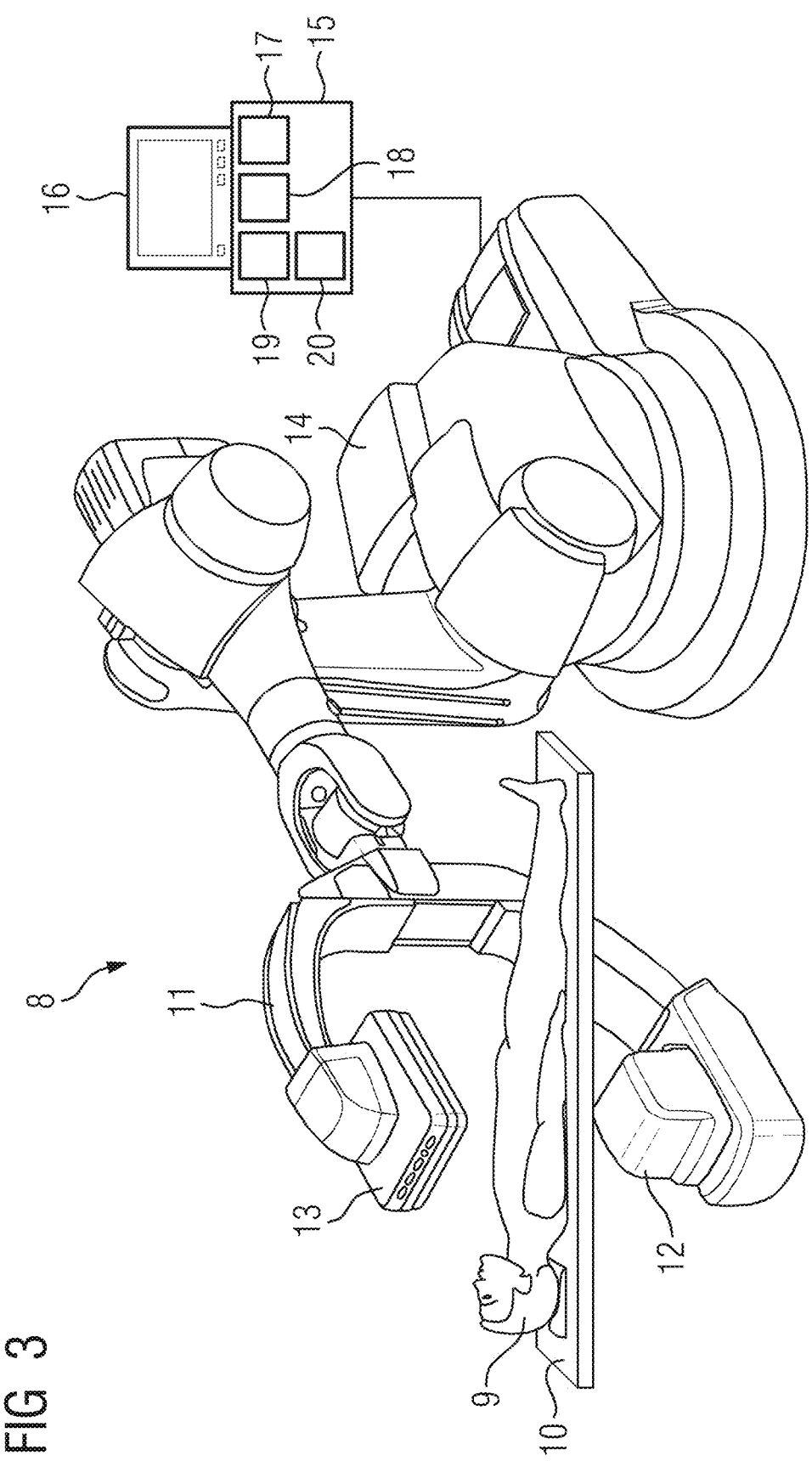
FIG. 3 shows an inventive x-ray device.

FIG. 3 finally shows an example embodiment of an inventive x-ray device 8, such as can be used, for instance, on a workplace for a minimally invasive medical intervention, in which a patient 9 is placed on a patient couch 10. The x-ray device 8 has a C-arm 11, on which an x-ray emitter 12 and an x-ray detector 13 are arranged opposingly as a recording arrangement. The C-arm 11 is at present coupled here to a robot arm 14 as a stand, wherein other embodiments are naturally also conceivable.

Operation of the x-ray device 8 is controlled by way of a control device 15, which is at present also assigned a display device 16, for instance a monitoring monitor. The control device 15 is embodied to carry out the inventive method, for which purpose, aside from a recording unit 17 controlling the recording operation according to selected recording parameters, it also has a comparison unit 18 for determining the change in image contents (possibly also the change in image contents gradients) and an adjustment unit 19 for adjusting the recording dose. Furthermore, a communication unit 20 for determining a display image by combining a number of fluoroscopy images is also shown. Other subunits are naturally also conceivable.

Although the invention has been illustrated and described in detail with the preferred example embodiment, the invention is not restricted by the examples disclosed and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS 1 timeline
2 recording time instant
3 curve
4 time instant
5 base dose
6 value
7 bracket
8 x-ray device
9 patient
10 patient couch
11 C-arm
12 x-ray emitter
13 x-ray detector
14 robot arm
15 control device
16 display device
17 recording unit
18 comparison unit
19 adjustment unit
20 communication unit
S1-S7 step

What is claimed is:

1. A method for operating an x-ray device, the method comprising:
   acquiring fluoroscopy images of a patient with a recording rate and a recording dose;
   displaying the fluoroscopy images acquired to a user on a display device at a frame rate, the recording dose being selected automatically as a function of a change in image contents between consecutive fluoroscopy images acquired;

determining a display image, with a reduction in the recording dose from each of a number of fluoroscopy images recorded consecutively, corresponding to a maximally usable base dose; and outputting the display image determined to the display device.

2. The method of claim 1, wherein the frame rate is reduced when display images are determined.

3. The method of claim 1, wherein the recording dose is selected as a function of a gradient of a change in image contents using more than two fluoroscopy images recorded consecutively.

4. The method of claim 2, wherein a change in recording dose is changed in discrete stages as a function of a rearrangement threshold being exceeded or not met by the change in image contents.

5. The method of claim 4, wherein, with more than two stages, at least one stage is skipped upon at least one threshold value being exceeded by a change in image content gradients.

6. The method of claim 1, wherein a comparison measure, between two most up to date fluoroscopy images selected in an application-related manner, is selected as a measure of the change in image contents.

7. The method of claim 1, wherein the fluoroscopy images for monitoring a minimally invasive intervention carried out with an instrument are recorded.

8. An x-ray device, comprising:
a controller, operatively connected to a memory, to:
acquire fluoroscopy images of a patient at a recording rate and a recording dose; and
a display device to display the fluoroscopy images acquired to a user at a frame rate, the recording dose being selected automatically as a function of a change in image contents between consecutive fluoroscopy images acquired,
the controller being further configured to
determine a display image, with a reduction in the recording dose from each of a number of fluoroscopy images recorded consecutively, corresponding to a maximally usable base dose; and
output the display image determined to the display device.

9. A non-transitory computer program product, storing a computer program to, when executed by a controller of an x-ray device, performs the method of claim 1.

10. A non-transitory electronically readable data carrier, storing a computer program to, when executed by a controller of an x-ray device, performs the method of claim 1.

11. The method of claim 1, wherein the method is for operating the x-ray device for recording a series of images for fluoroscopic monitoring of a recording region of the patient.

12. The method of claim 2, wherein the frame rate is reduced by a factor according to a number of combined fluoroscopy images with disjointed groups of fluoroscopy images to be combined.

13. The method of claim 1, wherein the recording dose is selected as a function of a gradient of a change in image contents using more than two fluoroscopy images recorded consecutively.

14. The method of claim 1, wherein a change in recording dose is changed in discrete stages as a function of a rearrangement threshold being exceeded or not met by the change in image contents.

15. The method of claim 14, wherein, with more than two stages, at least one stage is skipped upon at least one threshold value being exceeded by a change in image content gradients.

16. The method of claim 7, wherein the instrument is at least one of a catheter and a contrast agent propagation within the patient.

* * * * *